United States Patent [19]

Takaishi et al.

[11] Patent Number: 4,504,464
[45] Date of Patent: Mar. 12, 1985

[54] 2,3-DIALKOXYPROPYL GLYCERYL ETHER AND ITS PREPARATION PROCESS AS WELL AS COSMETIC COMPOSITION CONTAINING SAME

[75] Inventors: Naotake Takaishi; Yoshiaki Inamoto, both of Utsunomiya; Kouichi Urata, Ichikai; Junichi Kawano, Sakura; Hisao Tsutsumi, Miyashiro, all of Japan

[73] Assignee: Kao Soap Co., Ltd., Tokyo, Japan

[21] Appl. No.: 391,834

[22] Filed: Jun. 24, 1982

[30] Foreign Application Priority Data

Jul. 20, 1981 [JP] Japan .................................. 56-113404

[51] Int. Cl.$^3$ ...................... A61K 7/021; A61K 7/025
[52] U.S. Cl. ......................................... 424/63; 424/64; 568/623; 568/624
[58] Field of Search .................... 568/623, 624; 424/64

[56] References Cited

U.S. PATENT DOCUMENTS

| | | | |
|---|---|---|---|
| 2,695,915 | 11/1954 | De Groote | 568/623 |
| 3,398,201 | 8/1968 | Glickman. | |
| 3,595,924 | 7/1971 | Kalopissis et al. | 568/623 |
| 4,105,580 | 8/1978 | Sebag et al. | 568/624 |
| 4,224,311 | 9/1980 | Vanderberghe et al. | 424/64 |

FOREIGN PATENT DOCUMENTS 1484723  6/1967  France ............................... 568/624

Primary Examiner—Ethel G. Love
Attorney, Agent, or Firm—Oblon, Fisher, Spivak, McClelland & Maier

[57] ABSTRACT

Disclosed herein is a novel 2,3-dialkoxypropyl glyceryl ether and the preparation process for it. The above diglycerin dialkyl ether is readily prepared with high yield and purity by reacting its corresponding glycidyl ether with a protected glycerin to form a 1,3-dioxolan compound, followed by etherifying the thus formed 1,3-dioxolan compound into a dialkyl ether dioxolan compound, and then hydrolyzing the resultant dialkyl ether dioxolan compound. This diglycerin dialkyl ether is useful as an emulsifier, cleaner etc., and is preferably used as a component of cosmetic compositions. A cosmetic composition comprising the above 2,3-dialkoxypropyl glyceryl ether is also disclosed.

9 Claims, No Drawings

2,3-DIALKOXYPROPYL GLYCERYL ETHER AND ITS PREPARATION PROCESS AS WELL AS COSMETIC COMPOSITION CONTAINING SAME

BACKGROUND OF THE INVENTION

1. Field of the Invention

This invention relates to a novel 2,3-dialkoxypropyl glyceryl ether (hereinafter may be abbreviated as "diglycerin dialkyl ether") and its preparation process as well as a cosmetic composition containing same.

2. Description of the Prior Art

A number of polyalcohol derivatives containing one or more ether bonds therein are present in the nature. Among such polyalcohol derivatives, monoalkyl ethers of glycerin (called "glyceryl ethers") are particularly well-known. For example, fish lipids contain palmityl glyceryl ether (called "chimyl alcohol"), stearyl glyceryl ether (batyl alcohol) and oleyl glyceryl ether (selachyl alcohol).

These glyceryl ethers have found wide-spread commercial utility as base materials for cosmetic compositions, making use of their w/o emulsification characteristics (Japanese Patent Laid-open Nos. 87612/1974, 92239/1974, and 12109/1977, etc.). Besides, they are also known to have physiological activities such as erythropoietic stimmulating effect for bone marrow, anti-inflammatory effect and anti-tumor effect (Japanese Patent Publication Nos. 10724/1974 and 18171/1977).

Taking a hint from the fact that such glyceryl ethers are unique surfactants having numerous characteristic features, it has been attempted to derive from polyhydric alcohols polyol ether compounds having a molecular structure similar to these glyceryl ethers (in other words, containing one or more ether bonds and hydrophilic OH-groups within their molecules)—U.S. Pat. No. 2,258,892, Japanese Patent Publication No. 18170/1977, Japanese Patent Laid-open Nos. 137905/1978 and 145224/1979, etc. The thus-obtained polyol ether compounds are utilized as base materials for cosmetic compositions owing to their w/o emulsification characteristics (German Offenlegungsschrift No. 2,455,287) and, besides as general emulsifiers, antimicrobial and fungicidal agents.

SUMMARY OF THE INVENTION

An object of this invention is to provide a novel and useful polyol ether. This object is achieved by a diglycerin dialkyl ether represented by the general formula (I):

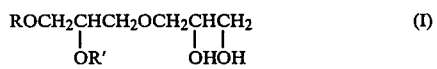

wherein R denotes a saturated or unsaturated, straight chain or branched, aliphatic hydrocarbon group containing 8–24 carbon atoms, and R' means a saturated or unsaturated, straight chain or branched, aliphatic hydrocarbon group containing 1–24 carbon atoms.

The novel diglycerin dialkyl ether according to this invention, which ether is represented by the general formula (I), is readily prepared with high yield and purity from its corresponding glycidyl ether having the general formula (V):

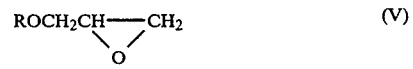

wherein R is a saturated or unsaturated, straight chain or branched, aliphatic hydrocarbon group containing 8–24 carbon atoms. The glycidyl ether of the general formula (V) can in turn be prepared easily from its corresponding alcohol.

For example, an intended diglycerin dialkyl ether of the general formula (I) may be prepared by reacting its corresponding glycidyl ether of the formula (V) with a glycerin (VI) whose 2,3-hydroxyl groups are protected by a suitable protecting group, i.e., an acetal or ketal of glycerin (hereinafter referred to as "protected glycerin") to form a 1,3-dioxolan compound (II), etherifying the thus-formed 1,3-dioxolan compound (II) into a dialkyl ether dioxolan compound (IV), and then hydrolyzing the resultant dialkyl ether dioxolan compound (IV). The above reactions are represented by the following reaction formulae:

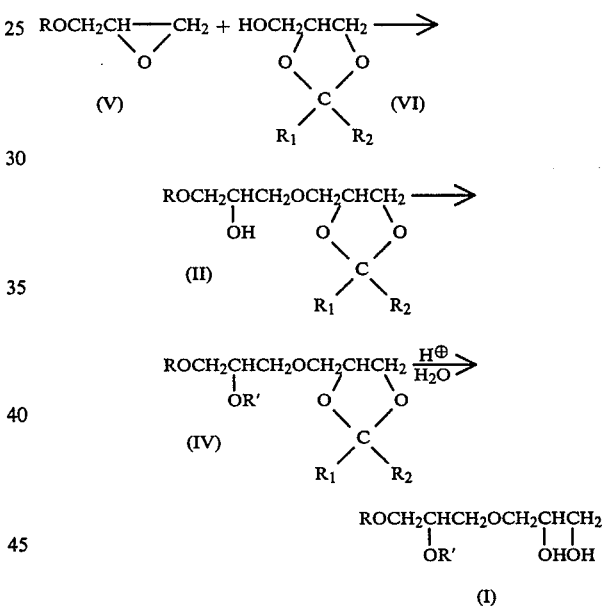

wherein R, R', $R_1$ and $R_2$ have the same significance as defined above.

The diglycerin dialkyl ether (I) according to this invention is chemically stable, develops little irritation to skin and pertains surface activity. Accordingly, it is useful as an emulsifier, cleaner, oil (emollient), self-emulsifying oil, wetting agent and thickener. It is preferably used, principally, as a component of cosmetic compositions.

DETAILED DESCRIPTION OF THE PREFERRED EMBODIMENT

The alkyl glycidyl ether (V) used as a starting material in the preparation process of this invention contains a saturated or unsaturated, straight chain or branched, aliphatic hydrocarbon group containing 8–24, and preferably 8–20 carbon atoms. As specific examples of such alkyl glycidyl ether (V), may be mentioned straight chain, primary alkyl glycidyl ethers such as n-octyl glycidyl ether, n-decyl glycidyl ether, n-dodecyl glycidyl ether, n-tetradecyl glycidyl ether, n-hexadecyl glycidyl ether, n-octadecyl glycidyl ether, n-octadecenyl glycidyl ether (oleyl glycidyl ether) and docosyl glycidyl ether; branched, primary alkyl glycidyl ethers such as 2-ethylhexyl glycidyl ether, 2-hexyldecyl glycidyl ether, 2-octyldodecyl glycidyl ether, 2-heptylundecyl glycidyl ether, 2-(1,3,3-trimethylbutyl)octyl glycidyl ether, 2-decyltetradecyl glycidyl ether, 2-dodecylhexadecyl glycidyl ether, 2-tetradecyl-octadecyl glycidyl ether, 5,7,7-trimethyl-2-(1,3,3-trimethylbutyl)octyl glycidyl ether and a methyl-branched isostearyl glycidyl ether represented by the following formula:

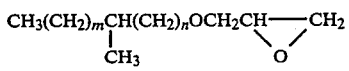

wherein m stands for integers ranging from 4 to 10, n means integers ranging from 5 to 11, m+n ranges from 11 to 17, and the methyl-branched isostearyl glycidyl ether has a distribution with a peak at m=7 and n=8; secondary alkyl glycidyl ethers such as sec-decyl glycidyl ether, sec-octyl glycidyl ether and sec-dodecyl glycidyl ether; and tertiary alkyl glycidyl ethers such as t-octyl glycidyl ether, and t-dodecyl glycidyl ether.

Incidentally, certain processes have recently been developed to prepare alkyl glycidyl ethers from their corresponding alcohols (ROH) with high yield without need for isolating their corresponding halohydrin ethers (see, for example, Japanese Patent Laid-open Nos. 76508/1979, 141708/1979, 141709/1979 and 141710/1979).

On the other hand, as the protected glycerine (VI), there are acetals of glycerin, which acetals are derived from aldehydes and ketals of glycerin which ketals are derived from ketones. As specific examples of compounds to be employed to form protecting groups, namely, aldehydes for converting glycerin into acetals, there may be mentioned aliphatic aldehydes (formaldehyde, acetaldehyde, propionaldehyde, octylaldehyde, etc.), alicyclic aldehydes (cyclopentylaldehyde, cyclohexylaldehyde, and the like), and aromatic aldehydes (benzaldehyde, naphthylaldehyde, etc.). On the other hand, exemplary ketones to obtain ketals may include aliphatic ketones (acetone, methyl ethyl ketone, diethyl ketone, methyl propyl ketone, dipropyl ketone, ethyl propyl ketone, methyl hexyl ketone, and the like), alicyclic ketones (cyclobutanone, cyclopentanone, cyclohexanone, cyclooctanone, etc.) and aromatic ketones (acetophenone, benzophenone, etc.). The preparation of protected glycerins from these compounds and glycerine can be carried out by subjecting glycerin and the above ketones or aldehydes to a dehydration/condensation reaction in the presence of an acidic catalyst in a manner known per se in the art.

As exemplary catalysts usable for the reaction between the alkyl glycidyl ether (V) and protected glycerin (VI), may be mentioned basic catalysts such as alkali metal hydroxides (for example, LiOH, NaOH, KOH, etc.), alkali metal alcoholates (for instance, NaOMe, NaOEt, t-BuOK and the like), tertiary amines (for example, triethylamine, tributylamine, tetramethyl ethylenediamine, tetramethyl-1,3-diaminopropane, tetramethyl-1,6-diaminohexane, triethylenediamine, etc.); and acidic catalysts including protonic acids such as sulfuric acid, hydrochloric acid, nitric acid, phosphoric acid and the like as well as Lewis acids such as boron trifluoride-ether complex, boron trifluoride-acetic acid complex, boron trifluoride-phenol complex, aluminum chloride, aluminum bromide, zinc chloride, tin tetrachloride, antimony chloride, titanium tetrachloride, silicon tetrachloride, ferric chloride, ferric bromide, cobaltic chloride, cobaltic bromide, zirconium chloride, boron oxide, activated acidic alumina, etc.

The above reaction is generally carried out by reacting an alkyl glycidyl ether (V) with a protected glycerin (VI) in a ratio of 1 mole to 1–10 moles, and preferably 1–5 moles in the presence of 0.001–0.02 mole, and particularly preferably 0.01–0.1 mole of a catalyst and at 70°–150° C., and particularly preferably 90°–120° C.

The protected glycerin (VI) may be used, theoretically speaking, in an equimolar amount with the alkyl glycidyl ether (V). Practically speaking, it is desirous to use the protected glycerin (VI) somewhat more than the equimolar amount for better yield and shorter reaction time. Although the reaction may still proceed without any reaction solvent, it is most appropriate to use the protected glycerin in an excess amount so that it can also serve as a reaction solvent. Alternatively, a reaction solvent may be additionally used if needed. Any solvent may be employed as a reaction solvent so long as it does not affect adversely on the present reaction. However, hydrocarbon solvents are suitable. Among such hydrocarbon solvents, there are aliphatic hydrocarbons such as pentane, hexane, heptane, octane and the like, aromatic hydrocarbons such as benzene, toluene, xylene, etc., alicyclic hydrocarbons such as cyclopentane, cyclohexane and the like, and mixtures thereof.

By carrying out the reaction as described above, the 1,3-dioxolan compound (II) can be obtained with a high yield of 80% or more. It may be purified by distillation or the like if needed. However, it can be furnished for the subsequent reaction as is without conducting its isolation and purification because it is usually obtained as colorless, odor-free, clear liquid.

The 1,3-dioxolan compound is then etherified into its corresponding dialkyl ether oxolan compound (IV). It is preferred to conduct this etherification reaction in the presence of an alkaline substance.

Exemplary alkaline substances may include alkali metal hydroxides, alkali metal carbonates, alkali metal phosphates, etc. Among these substances, alkali metal hydroxides such as sodium hydroxide and potassium hydroxide are particularly suitable from the industrial viewpoint. It is preferable to use such an alkaline substance in an amount of 1–10 moles per mole of the dioxolan compound (II) as a 10–80%, and more preferably 30–60% aqueous solution.

As etherification agents suitable for use in etherifying the 1,3-dioxolan compound (II), alkyl halides, alkyl sulfonates, alkyl sulfates and the like may be used. These etherification agents contain a saturated or unsaturated, straight chain or branched, aliphatic hydrocarbon group having 1–24, and preferably 1–18 carbon atoms. Accordingly, exemplary etherification agents include alkyl halides such as alkyl chlorides, alkyl bromides and alkyl iodides, alkyl para-toluene sulfonates, alkyl methane sulfonates, etc. Among such etherification agents, alkyl bromides and alkyl iodides may be mentioned as suitable etherification agents. As alkyl groups of such alkyl bromides and alkyl iodides, there may be mentioned, as straight chain aliphatic hydrocarbon groups, methyl, ethyl, propyl, butyl, octyl, decyl, hexadecyl, octadecyl, octadecenyl(oleyl), and the like; as branched aliphatic hydrocarbon groups, 2-ethylhexyl, 2-heptylundecyl, 5,7,7-trimethyl-2-(1,3,3-trimethylbutyl)octyl, a methyl-branched isostearyl group represented by the following formula:

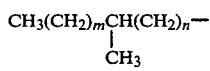

wherein m stands for integers ranging from 4 to 10, n means integers ranging from 5 to 11, m+n ranges 11 to 17, and the methyl branched isostearyl group has a distribution with a peak at m=7 and n=8, and the like; and as alicyclic hydrocarbon groups, cyclohexyl, cyclopentyl, cyclooctyl, etc. In addition, aromatic hydrocarbon groups may also be used but aliphatic hydrocarbon groups are particularly suitable in the present invention. The etherification agents may be employed in any proportions but are suitably used in an amount of 1-6 moles or so per mole of the dioxolan compound (II).

It is preferred to conduct the etherification reaction of the 1,3-dioxolan compound (II) in the presence of a catalytic amount of a quaternary onium salt. As such a quaternary onium salt usable at this stage, ammonium salts are preferred particularly for their availability in an industrial scale. As specific example of such quaternary ammonium salts, may be mentioned tetraalkylammonium salts (for example, tetrabutylammonium chloride, tetrabutylammonium hydrogensulfate, trioctylmethylammonium chloride, lauryltrimethylammonium chloride, stearyltrimethylammonium chloride, benzyltrimethylammonium chloride, etc.); a class of alkyl ammonium salts containing a polyoxyalkylene group (for instance, tetraoxyethylenestearyl dimethylammonium chloride, bis-tetraoxyethylenestearyl methylammonium chloride, and the like); as well as betaine compounds, crown ethers, amine oxide compounds, ion-exchange resins, etc. These quaternary onium salts may be used in a catalytic amount. More specifically, it is suitable to use them in an amount of 0.005-0.5 mole per mole of the dioxolan compound (II).

Furthermore, regarding the reaction solvent, anything may be employed unless it affects adversely on the present reaction. Among those particularly preferred, are included aliphatic hydrocarbons such as hexane, heptane and octane, alicyclic hydrocarbons such as cyclopentane and cyclohexane, and aromatic hydrocarbons such as benzene, toluene and xylene. Besides, ether compounds such as diethyl ether, THF, diglyme, dioxane and the like may equally be used.

The hydrolysis reaction of the dialkyl ether (IV) of the 1,3-dioxolan compound may be carried out in accordance with any methods known as hydrolysis methods for dioxolan. It is however preferred to conduct the hydrolysis reaction by using a protonic acid catalyst such as sulfuric acid, hydrochloric acid, nitric acid, phosphoric acid, benzene sulfonic acid or acetic acid and heating the dialkyl ether (IV) in water. There is no special limitation vested to the amount of the acid catalyst to be incorporated. A range of 0.01-2N is sufficient but a particularly suitable range is 0.05-1N. The hydrolysis reaction may be carried out by adding, to water, a water-soluble organic solvent for example a lower alcohol such as methanol, ethanol or isopropanol, THF, dioxane, or the like. A preferred reaction temperature ranges from 50° C. to 100° C.

Upon conducting the hydrolysis reaction under such conditions, the intended compound, diglycerin dialkyl ether (I) can be obtained substantially in a stoichiometric amount from the dialkyl ether dioxolan (IV).

Although it is most convenient and preferred to prepare the diglycerin dialkyl ether (I) of this invention in accordance with the above process, it may also be obtained by another process. Namely, following the below-described reaction formulae, the diglycerin dialkyl ether may be obtained by reacting an alcohol (VII) with an epoxide compound (VIII) of the 1,3-dioxolan type in the presence of an acidic or basic catalyst to form a 1,3-dioxolan compound (II) and then treating the 1,3-dioxolan compound (II) in a manner similar to that mentioned above.

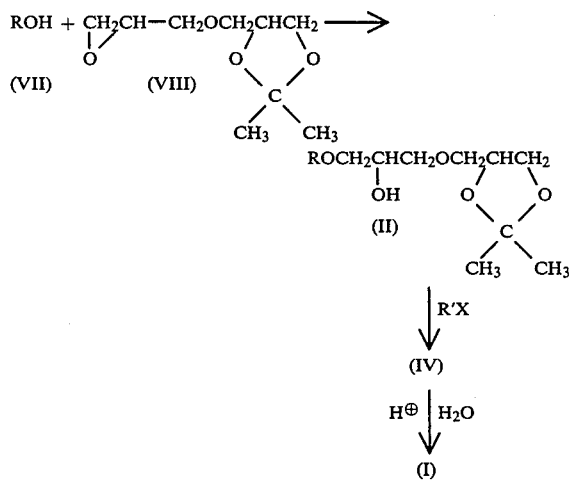

wherein R and R' have the same significance as defined above, and X is a halogen atom or the like.

The latter preparation route is however accompanied by a number of by-products which occur upon the formation of the 1,3-dioxolan compound (II) and the final diglycerin dialkyl ether (I) is thus insufficient in purity. Accordingly, the latter preparation route requires a further step such as distillation at the end thereof. The inventors tried to determine the chemical structure of the diglycerin dialkyl ether (I) obtained in accordance with this invention, using the diglycerin dialkyl ether resulted from the latter preparation route. It was in fact found that the intermediate compound, 1,3-dioxolan compound (II), had an extremely low level of yield, namely, about 30% or so when a basic catalyst was employed and about 35% or so when an acidic catalyst was relied upon (see, Comparative Examples 1-3).

Among all the 2,3-dialkoxypropyl glyceryl ethers represented by the general formula (I) according to this invention, those containing lower alkyl groups having 1-3 carbon atoms as R' are especially useful as emulsifiers for cosmetic compositions owing to their strong emulsification capacity. They show stronger nature as oil as the carbon number of R' becomes greater. 2,3-dialkoxypropyl glyceryl ethers containing 4-18 carbon atoms are especially useful as oily components for cosmetic compositions. Their contents in each cosmetic composition may vary depending on various parameters but about 0.2-15 wt% or so is preferred.

The invention will hereinafter be described in detail with reference to the following examples. However, it should be noted that the present invention shall not be limited thereto.

Preparation of alcohols, which serve as starting materials for glycidyl ethers, will also be given as Referential Examples.

REFERENTIAL EXAMPLE 1

Into a 1-liter, round-bottomed flask equipped with a reflux condenser, thermometer, dropping funnel and stirrer, were added 120 g of 50% aqueous solution of sodium hydroxide (60 g or 1.5 moles as pure sodium hydroxide), 68 g (0.25 mole) of monomethyl-branched isostearyl alcohol obtained in Referential Example 2, 200 ml of n-hexane and 2.51 g (0.0075 mole) of stearyl trimethylammonium chloride in the order as they have appeared above. The resulting reaction mixture was maintained at a reaction temperature of 25° C. in a water bath. While vigorously stirring the reaction mixture at a stirring speed of 400 r.p.m., 93 g (1 mole) of epichlorohydrin was dropped from the dropping funnel. After completing the dropwise addition of epichlorohydrin in the course of about 1.5 hours, the temperature of the reaction mixture was raised to 50° C., where it was stirred approximately for further 8 hours. Upon completion of the reaction, the reaction mixture was treated in the manner routinely employed in the art to obtain 68 g of monomethyl-branched isostearyl glycidyl ether represented by the following formula (yield: 33%).

Melting point: 142°-175° C. (0.08 mmHg).

IR (liquid film, cm$^{-1}$): 3050, 3000, 1250, 1100, 920, 845.

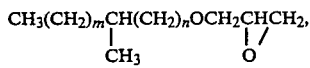

wherein m stands for integers ranging from 4–10, n means integers ranging from 5 to 11, m+n ranges 11 to 17, an the ether has a distribution with a peak at m=7, n=8.

REFERENTIAL EXAMPLE 2

Charged in a 20-liter autoclave, were 4770 g of isopropyl isostearate (Emery 2310 Isopropyl Isostearate, commercially available from Emery Industries Inc., U.S.A.) and 239 g of a copper-chromium catalyst (product of JGC Corporation). The flask was then filled with hydrogen gas at a pressure of 150 kg/cm$^2$ and the reaction mixture was then heated to 275° C. After carrying out the hydrogenation for about 7 hours under 150 kg/cm$^2$/275° C., the reaction product was cooled and the catalyst residue was filtered off, thereby obtaining a crude reaction product in an amount of 3500 g. Upon distilling the crude reaction product under reduced pressures, 3300 g of colorless, clear isostearyl alcohol was obtained as a 80°-167° C./0.6 mmHg fraction. The thus-obtained isostearyl alcohol (monomethyl-branched isostearyl alcohol) had an acid value of 0.05, saponification value of 5.5 and hydroxyl value of 181.4. Its IR analysis (liquid film) showed absorption at 3340 and 1055 cm$^{-1}$, while its NMR (CCl$_4$ solvent) analysis developed absorption at δ 3.50 (broad triplet, —CH$_2$—OH). From its gas chromatographic analysis, the main component of the isostearyl alcohol was found to be a mixture which consisted of about 75% of an isostearyl alcohol containing in total 18 carbon atoms in its alkyl group and the remainder of isostearyl alcohols respectively containing 14 and 16 carbon atoms as the total carbon numbers of their alkyl groups, each of the isostearyl alcohols containing its branched methyl group near the center of its main alkyl chain.

EXAMPLE 1

(1) Into a 1-liter reaction vessel equipped with a reflux condenser, thermometer, dropping funnel and stirrer, were placed 298 g (2.25 moles) of acetone glycerin ketal and 12.9 g (0.075 mole) of tetramethyl diaminohexane. They were mixed together. The reaction mixture was heated to 100° C., followed by a slow, dropwise addition of 140 g (0.75 mole) of octyl glycidyl ether from the dropping funnel. The temperature of the reaction mixture was maintained at 100°-110° C. during the dropwise addition of glycidyl ether. It took about 30 minutes until the dropwise addition of glycidyl ether was finished. Then, the reaction mixture was heated at 100°-110° C. for 6 hours. Subsequent to its cooling, excess acetone glycerin ketal, etc. were evaporated under reduced pressures from the reaction mixture. Upon subjecting the remainder to distillation under reduced pressures, 203 g of colorless, clear liquid was obtained (yield: 85%). Its gas chromatographic analysis showed a single peak, whereby confirming that the colorless, clear liquid was 2,2-dimethyl-4-(2'-hydroxy-3'-octoxy)-propoxymethyl-1,3-dioxolan.

Boiling point: 172°-175° C. (0.6 mmHg).

Elementary analysis: Calculated for C$_{17}$C$_{34}$O$_5$(%): C, 64.12; H, 10.76; O, 25.12. Found(%): C, 63.9; H, 10.8; O, 24.7.

IR (liquid film, cm$^{-1}$): 3470, 1380, 1370, 1255, 1212, 1110, 1080, 1050, 840

NMR (CCl$_4$ solvent, δ): 3.3–4.4 (multiplet, 13H,

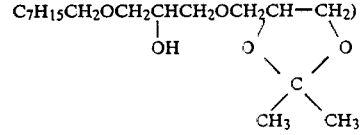

1.37 (singlet, 6H, —OCH$_2$CH—CH$_2$)

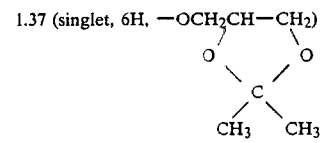

1.4 (broad singlet, 12H, CH$_3$(C$\underline{H_2}$)$_6$CH$_2$O—); 0.95 (triplet, 3H, C$\underline{H_3}$(CH$_2$)$_6$CH$_2$O—).

Acid value: 0.01 (found), 0.0 (calculated).
Saponification value: 0.03 (found), 0.0 (calculated).
Hydroxyl value: 180 (found), 176 (calculated).
Iodine value: 0.1 (found), 0.0 (calculated).
Oxirane oxygen: 0% (found), 0% (calculated).
Molecular weight (VPO method/CHCl$_3$): 318 (found), 318 (calculated).

(2) Added to a 1-liter reaction vessel equipped with a reflux condenser, thermometer, dropping funnel and stirrer were first 49.5 g of 97% NaOH (48 g, i.e., 1.2 moles as NaOH) and then 46.5 g of water to obtain a 50% aqueous NaOH solution, followed by further addition of 150 g of hexane and 63.7 g of 2,2-dimethyl-4-(2'-hydroxy-3'-octoxy)-propoxymethyl-1,3-dioxolan (0.2 mole) obtained in Procedure (1) of Example 1. Then, the resultant reaction mixture was agitated vigorously, followed by an addition of 3.4 g (0.01 mole) of tetrabutyl ammonium hydrogensulfate. The reaction mixture was maintained at 25° C., to which reaction mixture was dropped little by little 85.2 g (0.6 mole) of methyl iodide from the dropping funnel. Upon completion of the dropwise addition, the reaction mixture was heated to 50° C., where it was stirred approximately for further 5 hours. After confirming through a gas chromatographic analysis on the reaction mixture that the monoalkyl ether was not present any longer, the reaction mixture was cooled and decanted to collect the hexane layer. Subsequent to drying the thus-collected hexane layer with sodium sulfate, hexane was evaporated under reduced pressures. Thereafter, its distillation under reduced pressures gave 56.6 g of 2,2-dimethyl-4-(2'-methoxy-3'-octoxy)propoxymethyl-1,3-dioxolan as colorless, clear liquid (yield: 85%).

Boiling point: 154°–158° C. (0.7 mmHg).

Elementary analysis: Calculated for $C_{18}H_{36}O_5$ (%): C, 65.03; H, 10.91, O, 24.06. Found (%): C, 64.9; H, 10.8; O, 24.1.

IR (liquid film, cm$^{-1}$): 1380, 1370, 1260, 1213, 1115, 1055, 850.

NMR (CCl$_4$ solvent, TMS internal reference, δ): 3.1–4.3 (multiplet, 12H;

$$C_7H_{15}CH_2OCH_2\underset{OCH_3}{\overset{|}{C}H}CH_2OCH_2CH\underset{O\diagdown\phantom{C}\diagup O}{\overset{\diagup\phantom{C}\diagdown}{-}}CH_2)$$
$$\underset{CH_3\phantom{XX}CH_3}{\overset{\diagup\phantom{C}\diagdown}{C}}$$

3.35 (singlet, 3H; —OC$\underline{H}_3$); 1.30 (singlet, 6H;

$$-CH-CH_2)$$
$$O\diagdown\phantom{X}\diagup O$$
$$\underset{CH_3\phantom{XX}CH_3}{\overset{\diagup\phantom{C}\diagdown}{C}}$$

1.25 (broad singlet, 12H, CH$_3$(C$\underline{H}_2$)$_6$CH$_2$O—); 0.89 (triplet, 3H, C$\underline{H}_3$(CH$_2$)$_6$CH$_2$O—).

Acid value: 0.03 (found), 0.0 (calculated).
Saponification value: 0.05 (found), 0.0 (calculated).
Hydroxyl value: 0.10 (found), 0.0 (calculated).
Iodine value: 0.05 (found), 0.0 (calculated).
Oxirane oxygen: 0% (found), 0% (calculated).
Molecular weight (VPO method/CHCl$_3$): 335 (found), 332 (calculated).

(3) Two hundred milliliters (200 ml) of a 1N aqueous solution of sulfuric acid were charged into a 1-liter reaction vessel equipped with a reflux condenser, thermometer and stirrer, followed by further addition of 66.4 g (0.2 mole) out of the 2,2-dimethyl-4-(2'-methoxy-3'-octoxy)propoxymethyl-1,3-dioxolan obtained by repeating Procedure (2) of Example 1 twice and then 200 ml of ethanol. The reaction mixture was heated and refluxed with stirring. The reaction mixture looked like a milky, uneven emulsion in the beginning but, as soon as the refluxing started, it turned to a colorless, clear, uniform solution. It was heated and refluxed for about 6 hours and the resultant reaction mixture was cooled and neutralized by the addition of 8.3 g of 97% NaOH. After the neutralization, 300 ml of ether was added and the ether layer was collected through decantation. It was dried with sodium sulfate and its ether was driven off under reduced pressures. Thereafter, it was dried for about 3 hours under a reduced pressure of 0.1 mmHg at 100° C. Thus, 57 g of 2-methoxy-3-octoxypropyl glyceryl ether was resulted as colorless, clear, viscous liquid (yield: 98%).

Elementary analysis: Calculated for $C_{15}H_{32}O_5$ (%): C, 61.61; H, 11.03; O, 27.36. Found (%): C, 61.4; H, 11.0; O, 27.1.

IR (liquid film, cm$^{-1}$): 3400, 1000–1170, 850.

NMR (CCl$_4$ solvent, TMS internal reference, δ): 4.10 (singlet, 2H;

$$-OCH_2\underset{OH}{\overset{|}{C}H}\underset{OH}{\overset{|}{C}H_2})$$

3.41 (singlet, 3H; —OC$\underline{H}_3$); 3.10–3.90 (multiplet, 12H;

$$C_7H_{15}CH_2OCH_2\underset{OCH_3}{\overset{|}{C}H}CH_2OCH_2\underset{OH}{\overset{|}{C}H}\underset{OH}{\overset{|}{C}H_2})$$

1.3 (broad singlet, 12H; CH$_3$(C$\underline{H}_2$)$_6$CH$_2$O—); 0.88 (triplet, 3H; C$\underline{H}_3$(CH$_2$)$_6$CH$_2$O—)

Acid value: 0.01 (found), 0.0 (calculated)
Saponification value: 0.03 (found), 0.0 (calculated)
Hydroxyl value: 380 (found), 384 (calculated)
Iodine value: 0.0 (found), 0.0 (calculated)
Molecular weight (VPO method/CHCl$_3$): 290 (found), 292 (calculated).

EXAMPLE 2

(1) Procedure (1) of Example 1 was followed exactly except for the employment of 182 g (0.75 mole) of dodecyl glycidyl ether in place of octyl glycidyl ether. By effecting similar post treatment, 230 g of colorless, clear liquid was obtained (yield: 82%). A gas chromatographic analysis showed that the colorless, clear liquid consisted of a single component, namely, 2,2-dimethyl-4-(2'-hydroxy-3'-dodecyloxy)propoxymethyl-1,3-dioxolan.

Boiling point: 196°–200° C. (0.5 mmHg)

Elementary analysis: Calculated for $C_{21}H_{42}O_5$ (%): C, 67.34; H, 11.30; O, 21.36. Found (%): C, 67.0; H, 11.4; O, 21.1.

IR (liquid film, cm$^{-1}$): 3470, 1380, 1370, 1255, 1213, 1140, 1080, 1050, 845.

NMR (CCl$_4$ solvent, δ): 3.2–4.2 (multiplet, 12H;

$$C_{11}H_{23}CH_2OCH_2\underset{OH}{\overset{|}{C}H}-CH_2OCH_2CH\underset{O\diagdown\phantom{C}\diagup O}{\overset{\diagup\phantom{C}\diagdown}{-}}CH_2)$$
$$\underset{CH_3\phantom{XX}CH_3}{\overset{\diagup\phantom{C}\diagdown}{C}}$$

2.8 (singlet, 1H, $$C_{11}H_{23}CH_2OCH_2\underset{OH}{\overset{|}{C}H}-CH_2O-)$$

1.25 (singlet, 6H, $$-OCH_2CHCH_2)$$
$$O\diagdown\phantom{X}\diagup O$$
$$\underset{CH_3\phantom{XX}CH_3}{\overset{\diagup\phantom{C}\diagdown}{C}}$$

1.20 (broad singlet, 20H; CH$_3$(CH$_2$)$_{10}$CH$_2$O—); 0.87 (triplet, 3H; C$\underline{H}_3$(CH$_2$)$_{10}$CH$_2$O—).

Acid value: 0.0 (found), 0.0 (calculated).
Saponification value: 0.05 (found), 0.0 (calculated).
Hydroxyl value: 155 (found), 150 (calculated).
Iodine value: 0.3 (found), 0.0 (calculated).
Oxirane oxygen: 0% (found), 0% (calculated).
Molecular weight (VPO method/CHCl$_3$): 376 (found), 375 (calculated).

(2) Using 74.9 g (0.2 mole) of 2,2-dimethyl-4-(2'-hydroxy-3'-dodecyloxy)propoxymethyl-1,3-dioxolan obtained in Procedure (1) of Example 2, a reaction was carried out under the same conditions as those employed in Procedure (2) of Example 1. Similar post treatment provided 71.5 g of colorless, clear liquid (yield: 92%). A gas chromatographic analysis confirmed that it consisted of a single component, i.e., 2,2-dimethyl-4-(2'-methoxy-3'-dodecyloxy)propoxymethyl-1,3-dioxolan.

Boiling point: 180°–185° C. (0.4 mmHg).
Elementary analysis: Calculated for C$_{22}$H$_{44}$O$_5$ (%): C, 68.00; H, 11.41; O, 20.59; Found (%): C, 67.4; H, 11.4; O, 20.8.
IR (liquid film, cm$^{-1}$): 1380, 1370, 1260, 1216, 1115, 1050, 845.
NMR (CCl$_4$ solvent, TMS internal reference, δ): 3.2–4.3 (multiplet, 12H;

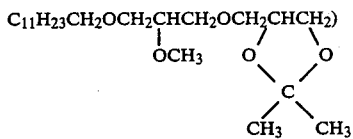

3.34 (singlet, 3H; —OC$\underline{H}_3$); 1.3 (singlet; 6H;

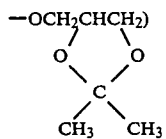

1.27 (broad singlet, 20H; CH$_3$(CH$_2$)$_{10}$CH$_2$O—); 0.85 (triplet, 3H; C$\underline{H}_3$(CH$_2$)$_{10}$CH$_2$O—).

Acid value: 0.10 (found), 0.0 (calculated).
Saponification value: 0.30 (found), 0.0 (calculated).
Hydroxyl value: 0.05 (found), 0.0 (calculated).
Iodine value: 0.20 (found), 0.0 (calculated).
Oxirane oxygen: 0% (found), 0% (calculated).
Molecular weight (VPO method/CHCl$_3$): 382 (found), 389 (calculated).

(3) Procedure (3) of Example 1 was exactly repeated except that 77.7 g (0.2 mole) out of the 2,2-dimethyl-4-(2'-methoxy-3'-dodecyloxy)propoxymethyl-1,3-dioxolan, which had been obtained by repeating Procedure (2) of Example 2 twice, was used to carry out its hydrolysis. The reaction mixture looked like a milky emulsion in the beginning of the reaction but it turned to a colorless, clear, uniform solution as soon as its refluxing started. Through similar post treatment, 68.3 g of 2-methoxy-3-dodecyloxypropyl glyceryl ether was resulted as colorless, clear, viscous liquid (yield: 98%).

Elementary analysis: Calculated for C$_{19}$H$_{40}$O$_5$ (%): C, 65.48; H, 11.57; O, 22.95. Found (%): C, 65.3; H, 11.2; O, 22.8.
IR (liquid film, cm$^{-1}$): 3400, 1000–1170, 850.
NMR (CCl$_4$ solvent, TMS internal reference, δ): 3.78 (singlet, 2H;

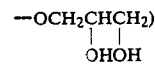

3.45 (singlet, 3H; —OC$\underline{H}_3$); 3.18–3.68 (multiplet, 12H;

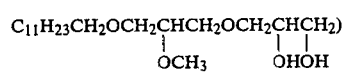

1.33 (broad singlet, 20H; CH$_3$(CH$_2$)$_{10}$CH$_2$O—); 0.89 (triplet, 3H; C$\underline{H}_3$(CH$_2$)$_{10}$CH$_2$O—).

Acid value: 0.03 (found), 0.0 (calculated).
Saponification value: 0.02 (found), 0.0 (calculated).
Hydroxyl value: 325 (found), 322 (calculated).
Iodine value: 0.0 (found), 0.0 (calculated).
Molecular weight (VPO method/CHCl$_3$): 350 (found), 349 (calculated).

EXAMPLE 3

(1) Into a 5-liter, round-bottomed flask equipped with a reflux condenser, thermometer, dropping funnel, nitrogen gas feed line and stirrer, were charged 1061 g (8 moles) of glycerin dimethyl ketal and 28.4 g (0.165 mole) of tetramethyl-1,6-diaminohexane. They were agitated and mixed under a nitrogen gas stream. While aerating the flask with nitrogen gas, 1308 g (4 moles) of the monomethyl-branched isostearyl glycidyl ether obtained in Referential Example 1 was dropped little by little from the dropping funnel. Here, the temperature of the reaction mixture was maintained around 100° C. by heating same during the dropwise addition of the glycidyl ether. The glycidyl ether was added in the course of about 2 hours, during which the temperature of the reaction mixture rose slowly and reached 125° C. when the dropping of the glycidyl ether was completed. The reaction mixture was then heated with stirring approximately for further 6 hours within a reaction temperature range of 130°–140° C. After confirming through a gas chromatographic analysis on the reaction mixture that all the isostearyl glycidyl ether had been used up, 1500 g city water and then 100 g of salt were successively added. The resultant mixture was allowed to stand and then decanted. The upper layer was collected through the decantation, dried with sodium sulfate, and then distilled under reduced pressures to drive off the glycerin dimethyl ketal which was used in an excess amount, thereby obtaining 1510 g of 2,2-dimethyl-4-(2'-hydroxy-3'-isostearoxy)propoxymethyl-1,3-dioxolan (yield: 82%).

Boiling point: 210°–230° C. (0.5–0.8 mmHg).
Elementary analysis: Calculated for C$_{27}$H$_{54}$O$_5$ (%): C, 70.62; H, 11.85; O, 17.42. Found (%): C, 70.7; H, 12.1; O, 16.9.
IR (liquid film, cm$^{-1}$): 3460, 1380, 1370, 1260, 1210, 1115, 1055, 850.
NMR (CCl$_4$ solvent, TMS internal reference, δ): 3.2–4.3 (multiplet, 12H;

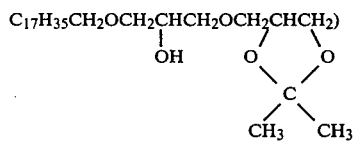

1.3 (singlet, 6H;

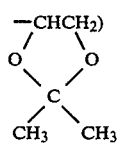

Acid value: 0.01 (found), 0.0 (calculated).
Saponification value: 1.5 (found), 0.0 (calculated).
Hydroxyl value: 120 (found), 122 (calculated).
Iodine value: 1.0 (found), 0.0 (calculated).
Oxirane oxygen: 0% (found), 0% (calculated).
Molecular weight (VPO method/CHCl$_3$): 458 (found), 459 (calculated).

(2) Charged in a 3-liter reaction vessel equipped with a reflux condenser, thermometer, dropping funnel and stirrer were 240 g of a 50% aqueous solution of sodium hydroxide (120 g, i.e., 3.0 moles of sodium hydroxide), 460 g of hexane, 8.5 g (0.025 mole) of tetrabutyl ammonium hydrogensulfate, and 230 g (0.5 mole) of the 2,2-dimethyl-4-(2'-hydroxy-3'-isostearoxy)propoxymethyl-1,3-dioxolan obtained in Procedure (1) of Example 3. They were then vigorously agitated at room temperature, followed by a dropwise slow addition of 142 g (1.0 mole) of methyl iodide from the dropping funnel. The reaction temperature was kept at room temperature during the dropping of methyl iodide. After completing the addition of methyl iodide, the reaction mixture was heated and refluxed. Upon completion of a heating and refluxing operation for about 6 hours, the reaction mixture was subjected to a gas chromatographic analysis to confirm that the 1,3-dioxolan compound (II) had been entirely used up. Thereafter, the reaction mixture was cooled down to room temperature, allowed to stand, and decanted. After collecting the organic layer, the water layer was extracted with hexane. The hexane layer was combined with the organic layer which had been obtained in advance. The solvents were evaporated under reduced pressures. A further distillation under reduced pressures gave 201 g of 2,2-dimethyl-4-(2'-methoxy-3'-isostearoxy)propoxymethyl-1,3-dioxolan as colorless, clear liquid (yield: 85%).

Boiling point: 196°–228° C. (0.6–0.8 mmHg).
Elementary analysis: Calculated for C$_{28}$H$_{56}$O$_5$ (%): C, 71.14; H, 11.86; O, 16.92. Found (%): C, 71.0; H, 11.8; O, 17.1.

IR (liquid film, cm$^{-1}$): 1380, 1370, 1260, 1210, 1110, 1050, 850.

NMR (CCl$_4$ solvent, TMS internal reference, δ): 3.2–4.3 (multiplet, 12H;

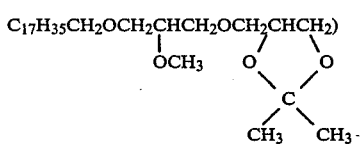

3.35 (singlet, 3H; —OC$\underline{H}_3$); 1.3 (singlet, 6H;

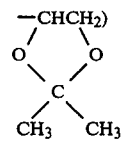

Acid value: 0.12 (found), 0.0 (calculated).
Saponification value: 0.4 (found), 0.0 (calculated).
Hydroxyl value: 0.5 (found), 0 (calculated).
Iodine value: 0.5 (found), 0.0 (calculated).
Oxirane oxygen: 0% (found), 0% (calculated).
Molecular weight (VPO method/CHCl$_3$): 471 (found), 473 (calculated).

(3) Into a 1-liter reaction vessel equipped with a reflux condenser, thermometer and stirrer, were successively added 120 g (0.25 mole) of 2,2-dimethyl-4-(2'-methoxy-3'-isostearoxy)propoxymethyl-1,3-dioxolan obtained in Procedure (2) of Example 3 and then 200 ml of methanol and 200 ml of a 1N aqueous sulfuric acid solution. They were refluxed under heating and stirring. After refluxing them for about 6 hours, it has been found from a gas chromatogram obtained on the reaction mixture that the hydrolysis of the dialkyl ether dioxolan compound (IV) had proceeded completely. The reaction mixture was cooled to room temperature, added with 500 ml of ether and then shaken. It was then allowed to stand to undergo decantation. The resulting ether layer was collected. Ether was evaporated from the ether layer under reduced pressures and the residue was dried approximately for 3 hours at 100° C./0.1 mmHg. Thus, 104 g of 2-methoxy-3-isostearoxypropyl glyceryl ether was obtained in a colorless, clear, syrupy state (yield: 96%).

Elementary analysis: Calculated for C$_{25}$H$_{52}$O$_5$ (%): C, 69.40; H, 12.11; O, 18.49. Found (%): C, 69.2; H, 12.0; O, 18.0.

IR (liquid film, cm$^{-1}$): 3400, 1040–1180.
NMR (CCl$_4$ solvent, TMS internal reference, δ): 3.3–3.8 (multiplet, 12H;

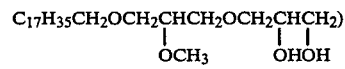

3.5 (singlet, 3H; —OC$\underline{H}_3$).
Acid value: 0.1 (found), 0.0 (calculated).
Saponification value: 0.5 (found), 0.0 (calculated).
Hydroxyl value: 250 (found), 260 (calculated).
Iodine value: 1.0 (found), 0.0 (calculated).
Oxirane oxygen: 0% (found), 0% (calculated).
Molecular weight (VPO method/CHCl$_3$): 435 (found), 433 (calculated).

EXAMPLE 4

Procedure (2) of Example 3 was repeated except that 184 g (1 mole) of n-butyl iodide was employed in lieu of methyl iodide. The reaction mixture was allowed to undergo a reaction at 65°–70° C. for about 20 hours. Through decantation, an organic layer was collected from the reaction mixture. Its solvent was then driven off under reduced pressures. Then, the residue was distilled under reduced pressures, resulting in the provision of 210 g of 2,2-dimethyl-4-(2'-butoxy-3'-isostearoxy)propoxymethyl-1,3-dioxolan as colorless, clear liquid (yield: 82%).

Boiling point: 210°–250° C. (0.7 mmHg).

Elementary analysis: Calculated for $C_{31}H_{62}O_5$ (%): C, 72.32; H, 12.14; O, 15.54. Found (%): C, 72.1; H, 12.0; O, 15.0.

IR (liquid film), cm$^{-1}$: 1380, 1370, 1260, 1207, 1110, 1060, 845.

NMR (CCl$_4$ solvent, TMS internal reference, δ): 3.2–4.2 (multiplet, 14H;

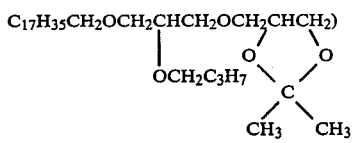

1.3 (singlet, 6H;

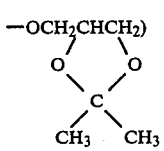

Acid value: 0.10 (found), 0.0 (calculated).
Saponification value: 0.5 (found), 0.0 (found).
Hydroxy value: 0.5 (found), 0.0 (calculated).
Iodine value: 0.3 (found), 0.0 (calculated).
Oxirane oxygen: 0% (found), 0% (calculated).
Molecular weight (VPO method/CHCl$_3$): 517 (found), 515 (calculated).

(2) Hydrolysis was effected on 134 g (0.26 mole) of 2,2-dimethyl-4-(2'-butoxy-3'-isostearoxy)propoxymethyl-1,3-dioxolan obtained in Procedure (1) of Example 4 in the same manner as in Procedure (3) of Example 3. After carrying out similar post treatment, 120 g of colorless, clear, syrupy 2-butoxy-3-isostearoxypropyl glyceryl ether was obtained (yield: 97%).

Elementary analysis: Calculated for $C_{28}H_{58}O_5$ (%): C, 70.84; H, 12.31; O, 16.85. Found (%): C, 70.7; H, 12.4; O, 16.8.

IR (liquid film, cm$^{-1}$): 3400, 1040–1180.

NMR (CCl$_4$ solvent, TMS internal reference, δ): 3.2–3.8 (multiplet, 14H;

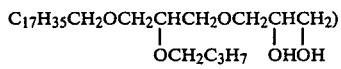

Acid value: 0.01 (found), 0.0 (calculated).
Saponification value: 0.2 (found), 0.0 (calculated).
Hydroxyl value: 235 (found), 236 (calculated).
Iodine value: 0.3 (found), 0.0 (calculated).
Oxirane oxygen: 0% (found), 0% (calculated).
Molecular weight (VPO method/CHCl$_3$): 474 (found), 475 (calculated).

EXAMPLE 5

(1) Procedure (2) of Example 3 was repeated except that 193 g (1 mole) of n-octyl bromide was employed in place of methyl iodide. It was reacted at 70°–75° C. for about 20 hours. An organic layer was collected through decantation from the reaction mixture and its solvent was driven off under reduced pressures. The residue was distilled under reduced pressures, thereby providing 257 g of 2,2-dimethyl-4-(2'-octoxy-3'-isostearoxy)propoxymethyl-1,3-dioxolan as colorless, clear liquid (yield: 90%).

Boiling point: 240°–270° C. (0.6–0.7 mmHg).
Elementary analysis: Calculated for $C_{35}H_{70}O_5$ (%): C, 73.63; H, 12.36; O, 14.01. Found (%): C, 73.9; H, 12.5; O, 14.3.

IR (liquid film, cm$^{-1}$): 1380, 1370, 1260, 1214, 1105, 1055, 845.

NMR (CCl$_4$ solvent, TMS internal reference, δ): 3.2–4.2 (multiplet, 14H;

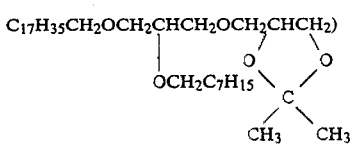

1.3 (singlet, 6H;

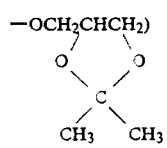

Acid value: 0.1 (found), 0.0 (calculated).
Saponification value: 0.3 (found), 0.0 (calculated).
Hydroxyl value: 0.0 (found), 0.0 (calculated).
Iodine value: 0.1 (found), 0.0 (calculated).
Oxirane oxygen: 0% (found), 0% (calculated).
Molecular weight (VPO method/CHCl$_3$): 573 (found), 571 (calculated).

(2) Hydrolysis was effected on 171 g (0.3 mole) of 2,2-dimethyl-4-(2'-octoxy-3'-isostearoxy)propoxymethyl-1,3-dioxolan obtained in Procedure (1) of Example 5 in the same manner as in Procedure (3) of Example 3. Upon carrying out post treatment in much the same way, 155 g of colorless, clear, syrupy 2-octoxy-3-isostearoxypropyl glyceryl ether was resulted (yield: 97.5%).

Elementary analysis: Calculated for $C_{32}H_{66}O_5$ (%): C, 72.40; H, 12.53; O, 15.07. Found (%): C, 72.8; H, 12.7; O, 14.6.

IR (liquid film, cm$^{-1}$): 3400, 1020–1170.

NMR (CCl$_4$ solvent, TMS internal reference, δ): 3.2–3.8 (multiplet, 14H;

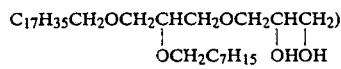

Acid value: 0.02 (found), 0.0 (calculated).
Saponification value: 0.1 (found), 0.0 (calculated).
Hydroxyl value: 205 (found), 210 (calculated).
Iodine value: 0.3 (found), 0.0 (calculated).
Oxirane oxygen: 0% (found), 0% (calculated).
Molecular weight (VPO method/CHCl$_3$): 533 (found), 531 (calculated).

COMPARATIVE EXAMPLE 1

In a 3-liter reaction vessel equipped with a reflux condenser, thermometer, dropping funnel and stirrer, were placed 720 g of a 50% aqueous solution of potassium hydroxide (360 g, i.e., 9 moles, as potassium hydroxide), 400 g of hexane, and 397 g (3 moles) of acetone glycerin ketal. They were vigorously agitated. Thereafter, 39.6 g (0.15 mole) of trimethyldodecylammonium chloride was added, followed by maintaining the reaction mixture at 30° C. Then, 555 g (6 moles) of epichlorohydrin was dropped little by little from the dropping funnel. It took about two hours until the entire epichlorohydrin was dropped. The reaction mixture was then heated to 50° C. and stirred under heating at the same temperature for approximately further 2 hours. The resulting reaction mixture was cooled and decanted. The thus-obtained hexane layer was dried with sodium sulfate and hexane was then driven off. The residue was thereafter subjected to distillation under reduced pressures, resulting in 440 g of the intended 2,2-dimethyl-4-(2',3'-epoxy)propoxymethyl-1,3,-dioxolan (yield: 78%).

Boiling point: 91°-94° C. (2.5 mmHg)—Literature value: 92°-94° C./2.5 mmHg [J. F. Prak. Chemie, 316, 325–336 (1974)].

COMPARATIVE EXAMPLE 2

In a 1-liter reaction vessel equipped with a reflux condenser, thermometer, dropping funnel and stirrer, were placed 117 g (0.9 mole) of octyl alcohol and 5.2 g (0.03 mole) of tetramethyl diaminohexane. They were heated to 100° C. and mixed together. Then, 56.5 g (0.3 mole) of 2,2-dimethyl-4-(2',3'-epoxy)porpoxymethyl-1,3-dioxolan obtained in the above Comparative Example 1 was added slowly from the dropping funnel. During the dropping period, the reaction mixture was maintained within a temperature range of 100°-110° C. They were allowed to react each other for about 6 hours within the same temperature range. The resulting reaction mixture was cooled, neutralized with dilute hydrochloric acid, and decanted to collect an organic layer. Upon carrying out distillation under reduced pressures, 29 g of colorless, clear liquid was resulted (yield: 31%). Its boiling point, gas chromatogram, IR spectrum and NMR spectrum were in conformity with their corresponding data obtained on the 1,3-dioxolan compound resulted in Procedure (1) of Example 1 which relates to the present invention.

COMPARATIVE EXAMPLE 3

The procedure of Comparative Example 2 was repeated except for the substitution of 4.2 g (0.03 mole) of boron trifluoride-ether complex for tetramethyl diaminohexane which was used as a catalyst. Upon carrying out distillation under reduced pressures, 33.4 g of colorless, clear liquid was obtained (yield: 35%). Its boiling point, gas chromatogram, IR spectrum and NMR spectrum coincided with their corresponding data on the 1,3-dioxolan compound obtained in Procedure (1) of Example 1 which relates to the present invention.

EXAMPLE 6

Physical and chemical properties of the compound prepared in Example 1, which compound relates to the present invention, and an example of its application for cosmetic compositions will be described below.

| Viscosity | Water-solubility (25°) | |
|---|---|---|
| (27° C.) | 10%* | 50%* |
| 423 cp | Dissolved | Dissolved |

* Content (%) of the diglycerin dialkyl ether according to this invention. These figures will have the same significance in subsequent examples.

An emulsion having the following composition was formulated:

| | | |
|---|---|---|
| A | Liquid paraffin | 14.0 (wt. %) |
| | Squalane | 14.0 |
| | 2-Methoxy-3-octoxypropyl glyceryl ether (this invention) | 2.0 |
| B | Sodium benzoate | 0.2 |
| | Glycerin | 4.0 |
| | Purified water | Balance |

All the components in Group A were mixed and heated to 75° C. All the components in Group B were mixed and heated to 70° C. on the side. Thus-mixed and heated components in Group B were then added to the mixture of the components in Group A while stirring the latter and carrying out emulsification. Then, the resultant mixture was cooled with stirring to room temperature, resulting in an emulsion.

The thus-obtained emulsion was w/o-type emulsified cream. It had extremely good stability as an emulsion and developed no separation over a long period of time. When applied to skin, it was very compatible with skin and was easy and comfortable to apply. Thus, the emulsion was suited as cosmetic cream.

EXAMPLE 7

Physical and chemical properties of the compound prepared in Example 2, which compound relates to the present invention, and an example of its application for cosmetic composition will be described below.

| Viscosity | Water-solubility (25° C.) | |
|---|---|---|
| (27° C.) | 10%* | 50%* |
| 504 cp | Dissolved | Liquid Crystal formed |

An emulsion having the following composition was formulated in a manner similar to that employed in Example 6.

| | |
|---|---|
| Spindle oil | 40.0 (wt. %) |
| Beef tallo | 12.0 |
| 2-Methoxy-3-dodecyloxypropyl glyceryl ether (this invention) | 3.2 |
| Purified water | Balance |

The resultant emulsion was a w/o-type creamy emulsion. Emulsified particles had a very fine mean diameter as little as about 1 micrometer. It showed good stability as an emulsion over a prolonged time period and had excellent properties as a metal-machining oil.

EXAMPLE 8

Physical and chemical properties of the compound prepared in Example 3, which compound relates to the present invention, and an example of its application for cosmetic compositions will be described below.

| Viscosity | Water-solubility (25° C.) | |
|---|---|---|
| (27° C.) | 10%* | 50%* |
| 382 cp | Dispersed liquid crystal formed | Liquid crystal formed |

An emulsion having the following composition was formulated.

| | | |
|---|---|---|
| A | Liquid paraffin | 40 (wt. %) |
| | Carnauba wax | 3 |
| | Ceresine | 7 |
| | Bees wax | 5 |
| | Vaseline | 7 |
| | Lake pigment | 6 |
| | 2-Methoxy-3-isostearoxypropyl glyceryl ether (this invention) | 2 |
| B | Propylene glycol | 10 |
| | Purified water | 20 |

The components in Group A were heated and mixed uniformly, to which a solution obtained by heating and mixing the components in Group B was added. The resultant mixture was emulsified and then immediately poured into a mold and cooled there.

The thus-obtained emulsion was a somewhat soft, solid, w/o-type emulsion having milky gloss and, after formed into a stick, had excellent properties as lip stick.

EXAMPLE 9

Physical and chemical properties of the compound prepared in Example 4, which compound relates to the present invention, and an example of its application for cosmetic compositions will be described below.

| Viscosity (27° C.) | Water-solubility (25° C.) | |
|---|---|---|
| | 10%* | 50%* |
| 240 cp | Partially dispersed (looked like an emulsion) | Partially dispersed (looked like an emulsion) |

A mixture of the following composition was formulated.

| | | |
|---|---|---|
| Carnauba wax | 3 (wt. %) | |
| Ceresine wax | 6 | |
| Candelilla wax | 5 | |
| Bees wax | 6 | |
| Castor oil | 40 | |
| Oleyloleate | 26 | |
| Vaseline | 10 | |
| 2-Butoxy-3-isostearoxypropyl glyceryl ether (this invention) | 4 | |

All the above components were heated to 85° C. so that they were melted. After thoroughly mixing them together, the resultant mixture was poured into a mold and cooled there.

The resultant mixture was a translucent, soft solid and, when applied to skin, it spreaded smoothly without showing stickiness and showed good compatibility with skin. Thus, it had excellent properties as lip cream.

EXAMPLE 10

Physical and chemical properties of the compound prepared in Example 5, which compound relates to the present invention, and an example of its application for cosmetic compositions will be described below.

| Viscosity (27°) | Water-solubility (25° C.) | |
|---|---|---|
| | 10%* | 50%* |
| 280 cp | Undissolved | Undissolved |

A mixture of the following composition was formulated in the same manner as in Example 9.

| | |
|---|---|
| Carnauba wax | 3 (wt. %) |
| Ceresine wax | 10 |
| Microcrystalline wax | 5 |
| Castor oil | 36 |
| Squalane | 30 |
| 2-Octoxy-3-isostearoxypropyl glyceryl ether (this invention) | 3 |
| Titanium oxide | 8 |
| Micaceous titanium | 2 |
| Ultramarine | 3 |

The resultant mixture was a soft solid of a bluish white color and, when used as eye shadow, it was very compatible with skin and exhibited excellent properties.

What is claimed is:

1. A 2,3-dialkoxypropyl glyceryl ether represented by the general formula (I):

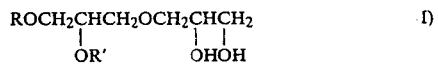

(I)

wherein R denotes a saturated or unsaturated, straight chain or branched, aliphatic hydrocarbon group containing 8–24 carbon atoms, and R' means a saturated or unsaturated, straight chain or branched, aliphatic hydrocarbon group containing 1–24 carbon atoms.

2. The 2,3-dialkoxypropyl glyceryl ether according to claim 1, wherein, in the general formula (I), R' means a lower alkyl group containing 1–3 carbon atoms and R denotes a saturated, straight chain or branched, aliphatic hydrocarbon group containing 8–20 carbon atoms.

3. The 2,3-dialkoxypropyl glyceryl ether according to claim 2, wherein R means octyl group.

4. The 2,3-dialkoxypropyl glyceryl ether according to claim 2, wherein R denotes dodecyl group.

5. The 2,3-dialkoxypropyl glyceryl ether according to claim 2, wherein R denotes a methyl-branched isostearyl group represented by the following formula:

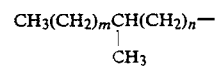

wherein m stands for integers ranging from 4 to 10, n means integers ranging from 5 to 11, m+n ranges from 11 to 17, and the methyl-branched isostearyl group has a distribution with a peak at m=7 and n=8.

6. The 2,3-dialkoxypropyl glyceryl ether according to claim 1, wherein, in the general formula (I), R denotes a methyl-branched isostearyl group represented by the following general formula:

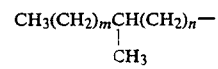

wherein m stands for integers ranging from 4 to 10, n means integers ranging from 5 to 11, m+n ranges from 11 to 17, and the methyl-branched isostearyl group has a distribution with a peak at m=7 and n=8, and R' contains 4–18 carbon atoms.

7. The 2,3-dialkoxypropyl glyceryl ether according to claim 6, wherein R' means butyl group.

8. The 2,3-dialkoxypropyl glyceryl ether according to claim 6, wherein R' means octyl group.

9. In a cosmetic composition, the improvement comprising 2,3-dialkoxypropyl glyceryl ether represented by the general formula (I):

$$ROCH_2CHCH_2OCH_2CHCH_2 \quad (I)$$
$$\quad\quad | \quad\quad\quad\quad | \ |$$
$$\quad\ OR' \quad\quad\quad OH\ OH$$

wherein R denotes a saturated or unsaturated, straight chain or branched, aliphatic hydrocarbon group containing 8–24 carbon atoms, and R' means a saturated or unsaturated, straight chain or branched, aliphatic hydrocarbon group containing 1–24 carbon atoms.

* * * * *